United States Patent [19]

Oshio et al.

[11] Patent Number: 4,918,171

[45] Date of Patent: Apr. 17, 1990

[54] SAIKOSAPONIN DERIVATIVES, THEIR PRODUCTION AND USE

[75] Inventors: Haruji Oshio, Hyogo; Noriaki Kawamura, Osaka; Taketoshi Saijo, Hyogo, all of Japan

[73] Assignee: Takeda Chemical Industries, Ltd., Osaka, Japan

[21] Appl. No.: 222,549

[22] Filed: Jul. 21, 1988

[30] Foreign Application Priority Data

Jul. 23, 1987 [JP] Japan .................................. 62-186463

[51] Int. Cl.$^4$ .................... C07G 3/00; C07J 15/24; A01N 43/04; A01N 45/00; A61K 31/705
[52] U.S. Cl. ..................................... 536/4.4; 536/4.1; 536/5
[58] Field of Search ................... 536/4.1, 4.4, 5, 6, 536/6.3; 514/25, 26

[56] References Cited

U.S. PATENT DOCUMENTS 3,629,231 12/1971 Hough et al. ..................... 536/4.1
4,101,652 7/1978 Bonati ............................... 536/4.4

FOREIGN PATENT DOCUMENTS 1567307 5/1980 United Kingdom ................... 536/5

*Primary Examiner*—Ronald W. Griffin
*Assistant Examiner*—Everett White
*Attorney, Agent, or Firm*—Wegner & Bretschneider

[57] ABSTRACT

A phosphate ester of saikosaponin a, $b_1$, $b_2$, c, d or h or saikogenin A, C or D, or a pharmaceutically acceptable salt thereof, which exhibits potent antiinflammatory activity against adjuvant arthritis and then can be used safely as a drug for the treatment and prevention of rheumatism, and a process for preparing the same characterized by phosphorylating the saikosaponin or saikogenin.

10 Claims, No Drawings

SAIKOSAPONIN DERIVATIVES, THEIR PRODUCTION AND USE

The present invention relates to phosphate esters of saikosaponins and saikogenins, which are compounds of use as highly useful drugs, and their production and use.

"Saiko" designates the dried roots of plants of the genus Bupleurum of the family Umbelliferae, such as *Bupleurum falcatum* L. "Saiko" is a Chinese drug, the principal indications of which are antipyresis and analgesia for flank pain and alternating cold and heat sensation, and it has been included in many traditional Chinese formulae. While "saiko" contains a series of oligogycosides having oleanane triterpenes as aglycones, which are collectively called saikogenin, its principal components are saiko-saponins a, c and d. However, in the course of drying and storage of the plants, the genuine saponins tend to sustain cleavage of the ether ring in the sapogenin moiety, partly giving rise to conjugated diene compounds such as saikosaponins $b_1$, h and $b_2$.

Inclusive of such conjugated diene compounds, all of these compounds will hereinafter be referred to collectively as saikosaponin or saikogenin.

Saikosaponin is known to have sedative, analgesic, antiinflammatory, antipyretic and other activities. Recently, an action to inhibit HeLa cells or L1210 leukemic factor has been found in the saponins formed upon partial acetylation of the sugar moieties of the glycosides.

However, there has not been the development, based on such findings, of any useful drug from saikosaponin or saikogenin.

The present invention provides a class of compounds of great utility as drugs, which are derived from saikosaponins a, $b_1$, $b_2$, c, d or h or saikogenins A, C or D by phosphorylation of one, two or three of the hydroxyl groups contained therein. Among the compounds of the invention are those compounds in which the phosphate moiety joins with another adjacent hydroxy group to form a cyclic phosphate ester. Furthermore, the phosphate moieties may form pharmaceutically acceptable salts with alkali metal or alkaline earth metals such as sodium, potassium, calcium and so on.

The processes for production of compounds of the invention are described below.

The compounds of the invention can be produced by phosphorylating any of the saikosaponins or saikogenins made available by the conventional technology or any protected derivatives thereof, such as isopropylidene-saikosaponin, acetylsaikosaponin, etc. wherein at least one hydroxyl group contained therein is free, with an appropriate phosphorylating agent, such as diphosphoryl chloride, phosphorus oxychloride, etc., and if desired, subjecting the resulting product to an ether ring-opening reaction, eliminating the remaining protective group or groups or/and converting into a salt in optional order.

PRODUCTION PROCESS (1)

The object compounds of the invention can be produced by reacting saikosaponin a, $b_1$, $b_2$, c, d or h or saikogenin A, C or D with a phosphorylating agent such as a diphosphoryl halide.

The diphosphoryl halide usable as such phosphorylating agent includes diphosphoryl chloride (hereinafter referred to briefly as DPC), diphosphoryl bromide, etc. but DPC is particularly desirable. While the level of addition of such phosphorylating agent is, of course, dependent on the species of compound to be produced, generally this reagent is used in a proportion of 1 to 10 equivalents, preferably 1 to 3 equivalents, per phosphate ester to be formed. This reaction is generally conducted in a solvent which is inert to the phosphorylating agent. For example, ethers such as tetrahydrofuran, dioxane and so on may be mentioned as examples of the solvent. The amount of the solvent is generally 5 to 200 ml, preferably 10 to 100 ml, per gram of the starting compound saikosaponin a, $b_1$, $b_2$, c, d or h or saikogenin A, C or D. The reaction temperature is $-70°$ C. to $0°$ C. and preferably $-40°$ C. to $-10°$ C. Depending on the species of starting compound, phosphorylating agent and solvent, reaction temperature and other conditions, the reaction generally goes to completion in a time ranging from 10 minutes to 10 hours. The resulting object compound of the invention can be isolated and purified by the known procedures such as chromatography, concentration under reduced pressure, pH adjustment, solvent extraction, crystallization and so on.

Taking saikosaponin $b_2$ as an example, this starting compound is first dissolved in 10 to 100 ml/g, preferably 20 to 50 ml/g, of tetrahydrofuran and DPC is added thereto gradually while the solution is maintained generally at $-70°$ to $0°$ C. and preferably at $-40°$ C. to $-10°$ C. While the required amount of DPC is dependent on the desired product compound, this reagent is used in a proportion of 1 to 10 equivalents, preferably 1.5 to 3 equivalents, for the formation of one equivalent of phosphate ester. The reaction mixture is stirred for 10 minutes to 5 hours, preventing a temperature build-up. Thereafter, water or an aqueous alkali solution such as aqueous sodium hydrogen carbonate solution is added. The above procedure provides the desired saikosaponin $b_2$ phosphate esters or salts thereof. This reaction product is usually a mixture of various phosphate esters of saikosaponin $b_2$ or salts thereof, and where the reaction product is a free acid, it can be converted in the conventional manner to a salt using an alkaline aqueous solution such as aqueous sodium hydrogen carbonate solution and, then, be fractionated and purified by column chromatography using a reverse phase support such as chemically bound silica gel, e.g. $C_8$, $C_{18}$ and so on. By way of illustration, where LiChroprep RP-8 or RP-18 (manufactured by Merck and Co., Inc. in U.S.A.) is used as the support, there can be fractionally recovered the salt of saikosaponin $b_2$-23,28,6''-tris(dihydrogen phosphate) from the fraction eluted with water to 1–15% (v/v) aqueous acetonitrile, the salt of saikosaponin $b_2$-28,6''-bis(dihydrogen phosphate) from the fraction eluted with 1–30% (v/v), preferably 1–2% (v/v) aqueous acetonitrile, the salt of saikosaponin $b_2$-23,6''-bis(dihydrogen phosphate) from the fraction eluted with 3–40% (v/v), preferably 3–8% (v/v) aqueous acetonitrile, and the salt of saikosaponin $b_2$-6''-(dihydrogen phosphate) from the fraction eluted with 15–50% (v/v), preferably 18–25% (v/v) aqueous acetonitrile.

The phosphorylation of saikosaponin $b_1$ with DPC in the same manner as described for saikosaponin $b_2$ gives rise to the phosphate esters of saikosaponin $b_1$ or salts thereof. This reaction product is usually a mixture of various phosphate esters of saikosaponin $b_1$ or salts thereof, and where the reaction product is a free acid, it can be converted in the conventional manner to a salt using, for example, an aqueous alkali solution and, then, be fractionated and purified by column chromatography using LiChroprep RP-8 or RP-18 as the support. In this case, there can be isolated the salt of saikosaponin $b_1$-cyclic 16,28-(hydrogen phosphate)-23,6"-bis(dihydrogen phosphate) from the fraction eluted with water to 1–20% (v/v) aqueous acetonitrile, the salt of saikosaponin $b_1$-cyclic 16,28-(hydrogen phosphate)-6"'-(dihydrogen phosphate) from the fraction eluted with 4–40% (v/v), preferably 4–10% (v/v) aqueous acetonitrile, and the salt of saikosaponin $b_1$-cyclic 16,28-(hydrogen phosphate) from the fraction eluted with 15–50% (v/v), preferably 15–25% (v/v) aqueous acetonitrile.

The phosphorylation of saikosaponin a in the same manner as described for saikosaponin $b_2$ gives rise to the phosphate esters of saikosaponin a or salts thereof. This reaction product usually is a mixture of two kinds of phosphate esters of saikosaponin a or salts thereof, and where the reaction product is in the form of the free acid, it can be converted in the conventional manner to a salt using, for example, an aqueous alkali solution and, then, fractionated and purified by column chromatography using LiChroprep RP-8 or RP-18 as the support. In this case, there can be isolated the salt of saikosaponin a-23,6"-bis(dihydrogen phosphate) from the fraction eluted with water to 1–40% (v/v), preferably 1–3% (v/v) aqueous acetonitrile and the salt of saikosaponin a-6"-(dihydrogen phosphate) from the fraction eluted with 6–50% (v/v), preferably 6–10% (v/v) aqueous acetonitrile.

The phosphorylation of saikosaponin d in the same manner as described for saikosaponin $b_2$ gives rise to the phosphate esters of saikosaponin d or salts thereof. This reaction product is usually a mixture of two kinds of phosphate esters of saikosaponin d or salts thereof, and where the reaction product is in the form of the free acid, it can be converted in the conventional manner to a salt using, for example, an aqueous alkali solution and, then, be fractionated and purified by column chromatography using LiChroprep RP-8 or RP-18 as the support. In this case, there can be isolated the salt of saikosaponin d-23,6"-bis(dihydrogen phosphate) from the fraction eluted with water to 1–40% (v/v), preferably 3–4% (v/v) queous acetonitrile and the salt of saikosaponin d-6"-(dihydrogen phosphate) from the fraction eluted with 13–50% (v/v), preferably 15–18% (v/v) aqueous acetonitrile.

The phosphorylation of saikosaponin h with DPC in the same manner as described for saikosaponin $b_2$ gives rise to the phosphate esters of saikosaponin h or salts thereof. This reaction product is usually a mixture of various phosphate esters of saikosaponin h or salts thereof, and where the reaction product is in the form of the free acid, it can be converted in the conventional manner to a salt using, for example, an aqueous alkali solution and, then, be fractionated and purified by column chromatography using LiChroprep RP-8 or RP-18 as the support. In this case, there can be isolated the salt of saikosaponin h-cyclic 16,28-(hydrogen phosphate)-3",6"'-bis(dihydrogen phosphate) from the fraction eluted with water to 1–20% (v/v), preferably 1–2% (v/v) aqueous acetonitrile, the salt of saikosaponin h-cyclic 16,28-(hydrogen phosphate)-6"'-(dihydrogen phosphate) from the fraction eluted with 3–30% (v/v), preferably 3–6% (v/v) aqueous acetonitrile, and the salt of saikosaponin h-cyclic 16,28-(hydrogen phosphate) from the fraction eluted with 5–40% (v/v), preferably 8–12% (v/v) aqueous acetonitrile.

The phosphorylation of saikosaponin c in the same manner as described for saikosaponin $b_2$ gives rise to the phosphate esters of saikosaponin c or salts thereof. This reaction product is usually a mixture of various phosphate esters of saikosaponin c or salts thereof, and where the reaction product is in the form of the free acid, it can be converted in the conventional manner to a salt using, for example, an aqueous alkali solution and, then, be fractionated and purified by column chromatography using LiChroprep RP-8 or RP-18 as the support. In this case, there can be isolated the salt of saikosaponin c-cyclic 2"',3"'-(hydrogen phosphate)-6"'-(dihydrogen phosphate) from the fraction eluted with water to 1–30% (v/v), preferably 1–3% (v/v) aqueous acetonitrile and the salt of saikosaponin c-6"'-(dihydrogen phosphate) from the fraction eluted with 5–40% (v/v), preferably 5–15% (v/v) aqueous acetonitrile.

The phosphorylation of saikogenin A in the same manner as described for saikosaponin $b_2$ generally gives rise to a mixture of various phosphate esters of saikogenin A or salts thereof, and where the reaction product is in the form of the free acid, it can be converted in the conventional manner to a salt using, for example, an aqueous alkali solution and, then, be fractionated and purified by column chromatography using LiChroprep RP-8 or RP-18 as the support. In this case, there can be isolated the salt of saikogenin A-cyclic 16,28-(hydrogen phosphate)-23-(dihydrogen phosphate) and the salt of saikogenin A-cyclic 3,23:16,28-bis(hydrogen phosphate) from the fraction eluted with water to 1–30% (v/v) aqueous acetonitrile and the salt of saikogenin A-cyclic 16,28-(hydrogen phosphate) from the fraction eluted with 2–50% (v/v), preferable 2–5% (v/v) aqueous acetonitrile.

The phosphorylation of saikogenin D in the same manner as described for saikosaponin $b_2$ generally gives rise to a mixture of various phosphate esters of saikogenin D or salts thereof. Where the reaction product is in the form of the free acid, it can be converted in the conventional manner to a salt using, for example, an aqueous alkali solution and, then, be fractionated and purified by column chromatography using LiChroprep RP-8 or RP-18 as the support. In this case, there can be isolated the salt of saikogenin D-23,28-bis(dihydrogen phosphate) and the salt of saikogenin D-cyclic 3,23-(hydrogen phosphate)-28-(dihydrogen phosphate) from the fraction eluted with water to 1–30% (v/v) aqueous acetonitrile and the salt of saikogenin D-23-(dihydrogen phosphate) and the salt of saikogenin D-cyclic 3,23-(hydrogen phosphate) from the fraction eluted with 2–50% (v/v), preferably 2–5% (v/v) aqueous acetonitrile.

The phosphorylation of saikogenin C in the same manner as described for saikosaponin $b_2$ gives rise to saikogenin C-cyclic 16,28-(hydrogen phosphate) or a salt thereof.

PRODUCTION PROCESS (2)

The phosphate ester of saikosaponin a, d or c or a salt thereof, prepared by production process (1), can be subjected to ether ring-opening reaction to give the object phosphate ester of saikosaponin $b_1$, $b_2$ or h or a salt thereof.

This ether ring-opening reaction can be accomplished, for example by allowing the compound to stand, with or without stirring, for example in an aqueous solution of mineral acid, such as 1 to 5% (w/v) hydrochloric acid, sulfuric acid, etc., or an 1 to 40% (w/w) aqueous solution of ferric chloride. The reaction temperature is generally 5° C. to 40° C. and preferably 10° C. to 30° C. This reaction can be carried through generally in 30 minutes to 24 hours. The resulting object compound of the present invention can be isolated and purified by the known procedures described hereinbefore.

For example, allowing saikosaponin d-6''-(dihydrogen phosphate) to stand in a 1 to 5% (w/v) aqueous solution of hydrochloric acid at 10° C. to 30° C. for 30 minutes to 24 hours gives saikosaponin $b_2$-6''-(dihydrogen phosphate).

Similarly, there can be obtained saikosaponin $b_2$-23,6''-bis(dihydrogen phosphate) from saikosaponin d-23,6''-bis(dihydrogen phosphate); saikosaponin $b_1$-6''-(dihydrogen phosphate) from saikosaponin a-6''-(dihydrogen phosphate); and saikosaponin $b_1$-23,6''-bis(dihydrogen phosphate) from saikosaponin a-23,6''-bis(dihydrogen phosphate). By the same fashion, there can be produced saikosaponin h-6'''-(dihydrogen phosphate) from saikosaponin c-6'''-(dihydrogen phosphate); and saikosaponin h-3'', 6'''-bis(dihydrogen phosphate) from saikosaponin c-cyclic 2'',3''-(hydrogen phosphate)-6'''-(dihydrogen phosphate).

PRODUCTION PROCESS (3)

The object compound of the invention can be produced by reacting saikosaponin a, $b_1$ or $b_2$ with 2,2-dimethoxypropane to give isopropylidenesaikosaponin a or diisopropylidenesaikosaponin $b_1$ or $b_2$, reacting the latter with a phosphorylating agent such as a diphosphoryl halide, a phosphorus oxyhalide or the like, and removing the isopropylidene group or groups.

This isopropylidene group-introducing reaction can be performed, for example by suspending saikosaponin a, $b_1$ or $b_2$ in 5 to 60 ml/g, preferably 10 to 50 ml/g, of 2,2-dimethoxypropane and adding thereto an organic acid such as p-toluenesulfonic acid or the like (0.005 to 1 g, preferably 0.01 to 0.5 g per gram of the substrate compound). The reaction is conducted generally at a temperature of $-10°$ C. to 70° C. and preferably at 0° C. to 30° C. Depending on the substrate compound, temperature and other conditions, the reaction time is generally in the range of 30 minutes to 14 hours. The resulting isopropylidene compound can be isolated by the known procedures such as the those mentioned hereinbefore or the reaction mixture as such can be submitted to the next phosphorylation reaction step. The phosphorylation reaction is accomplished by reacting this isopropylidene compound with a phosphorylating agent, such as diphosphoryl halides, phosphorus oxyhalides and so on. As said diphosphoryl halide, those mentioned under Production Process (1) can be employed. The phosphorus oxyhalide may for example be phosphorus oxychloride. The amount of such phosphorylating agent is generally 1 to 50 equivalents and preferably 5 to 30 equivalents per equivalent of the isopropylidene compound. The phosphorylating agent can be advantageously added to the reaction mixture obtained by the aforesaid isopropylidene group-introducing reaction or, alternatively, be subjected to reaction with the isopropylidene compound isolated from said reaction mixture in a solvent. As the type of solvent and reaction temperature and time, those mentioned under Production Process (1) can be adopted. After the phosphorylation reaction, water is added to the reaction mixture in a proportion of 10 to 200 ml, preferably 50 to 100 ml, per gram of the isopropylidene compound, and if necessary, an acid such as hydrochloric acid, sulfuric acid or the like is further added thereto for adjusting the mixture to pH 0 to 3, preferably pH 0.5 to 2, to thereby eliminate the isopropylidene group. The resulting object compound of the invention can be isolated and purified by the known procedures mentioned hereinbefore.

By way of example, diisopropylidenesaikosaponin $b_2$ can be produced by suspending saikosaponin $b_2$ in 10 to 50 ml/g, preferably 20 to 30 ml/g, of 2,2-dimethoxypropane, adding thereto 0.01 to 0.3 g, preferably 0.05 to 0.2 g, per gram of saikosaponin $b_2$, of an acid which is generally used for the introduction of an isopropylidene group to a hydroxy group, such as p-toluenesulfonic acid, and stirring the mixture for 1 to 8 hours at a constant temperature in the range of generally $-10°$ C. to 70° C. and preferably 0° C. to 30° C. When this compound is subjected to the aforementioned phosphorylation reaction with DPC and, then, the isopropylidene group of the reaction product is hydrolytically eliminated under acidic conditions (pH 0 to 3, preferably 0.5 to 2), there is obtained saikosaponin $b_2$-23-(dihydrogen phosphate). In the like manner, there can be obtained saikosaponin $b_1$-23-(dihydrogen phosphate) from saikosaponin $b_1$, or saikosaponin a-23-(dihydrogen phosphate) from saikosaponin a.

PRODUCTION PROCESS (4)

The object compound of the invention can be produced by reacting saikosaponin a, d or c with an acetylating agent, subjecting the fully acetylated compound to ether ring-opening reaction to give acetylated saiko saponin $b_1$, $b_2$ or h in which the hydroxy group in the 28 position only is free, reacting the same with a phosphorylating agent, and finally eliminating the acetyl groups.

The acetylating agent may for example be acetic anhydride for all practical purposes. The acetylating agent is used in a proportion of 5 to 30 ml, preferably 10 to 20 ml, per gram of saikosaponin a, d or c. The acetylation reaction is generally carried out in a solvent. For example, basic organic solvents such as pyridine, triethylamine, trimethylamine, etc. can be used. The amount of the solvent is 5 to 40 ml, preferably 10 to 25 ml, per gram of the starting compound. The acetylation reaction is conducted in the temperature range of generally 0° C. to 60° C. and preferably 10° C. to 50° C. Depending on the species of substrate compound, acetylating agent and solvent, temperature and other conditions, the reaction time is generally 1 to 48 hours and preferably 3 to 20 hours. The resulting fully acetylated derivative of saikosaponin a, d or c in which all the hydroxy groups have been acetylated can be isolated and purified by the known procedures described hereinbefore but generally the reaction mixture as such is directly submitted to the next ether ring-opening reaction step. The ether ring-opening reaction is accomplished by reacting the reaction mixture obtained by said acetylation reaction with an aqueous solution of mineral acid, such as a 1 to 40% (w/w) aqueous solution of ferric chloride or a 1 to 5% (w/v) aqueous solution of sulfuric acid or hydrochloric acid. The proportion of ferric chloride is 0.5 to 30 g, preferably 1 to 10 g, per gram of the fully acetylated derivative. The reaction temperature is generally 5° C. to 50° C. and preferably 10° C. to 40° C. Depending on the species of substrate compound, temperature and other conditions, the ether ring is cleaved open generally in 1 to 10 hours. Thus is obtained acetylated saikosaponin $b_1$, $b_2$ or h in which only the 28-hydroxy group is free, and this product compound can be isolated by the known procedures. Or the reaction mixture so obtained can be directly used as a starting material in the next phosphorylation reaction step. Thus, for example, the phosphorylation reaction can be accomplished by subjecting the reaction mixture obtained by the above ether ring-opening reaction to reaction with a diphosphoryl halide (such as DPC). The amount of such diphosphoryl halide should only be sufficient to phosphorylate the hydroxy group in the 28 position and is generally 1 to 10 equivalents. The reaction temperature and time may be the same as those mentioned under Production Process (1). After the phosphorylation reaction, the acetyl groups can be eliminated by subjecting the reaction mixture to hydrolysis reaction under alkaline conditions in the usual manner. The alkali used for this purpose includes hydroxides of alkali metals or alkaline earth metals, such as sodium hydroxide, potassium hydroxide, calcium hydroxide and so on. The alkali is used in an amount sufficient to assure that the hydrolytic deacetylation reaction system is maintained at pH 9 to 14, preferably 10 to 13. As regards water to be added, it is preferably used in large excess for all practical purposes. The reaction temperature is generally 5° C. to 70° C. and preferably 10° C. to 40° C. This deacylation reaction can be carried through generally in 1 to 20 hours. The resulting object compound of the invention can be isolated by the known procedures mentioned hereinbefore.

By way of example, the fully acetylated saikosaponin d can be obtained by adding 10 to 20 ml of acetic anhydride to a solution of saikosaponin d in 10 to 20 ml/g of pyridine and allowing the mixture to stand at 10° C. to 50° C. for 3 to 16 hours. When this reaction mixture is stirred with a 1 to 40% (w/w) aqueous solution of ferric chloride at 10° C. to 40° C. for 1 to 10 hours for cleavage of the ether ring, there is obtained the acetylated saikosaponin $b_2$ in which only the hydroxy group in the 28 position is free. This product is subjected to the above-described phosphorylation reaction with DPC and, then, to hydrolysis of the acetyl groups under alkaline conditions (pH 9-14, preferably pH 10-13), whereby the salt of saikosaponin $b_2$-28-(dihydrogen phosphate) is obtained. In the same manner as above, a salt of saikosaponin $b_1$-28-(dihydrogen phosphate) can be obtained from saikosaponin a, and a salt of saikosaponin h-28-(dihydrogen phosphate) from saikosaponin c.

PRODUCTION PROCESS (5)

The object compound of the invention can also be obtained by reacting saikosaponin a, d, $b_1$, $b_2$, c or h with a phosphorus oxyhalide.

As the phosphorus oxyhalide, phosphorus oxychloride (hereinafter referred to briefly as PC), for instance, can be usually employed. The amount of phosphorus oxyhalide is dependent on the species of desired product compound but is generally 1 to 10 equivalents and preferably 1 to 3 equivalents per phosphate ester to be formed. This phosphorylation reaction is preferably conducted in a solvent. As the solvent, basic organic solvents such as pyridine, quinoline, etc. can be used. Pyridine is among the preferred solvents. The reaction temperature is generally $-70°$ C. to $-10°$ C. and preferably $-40°$ C. to $-20°$ C. Dependent on the species of starting compound, phosphorylating agent and solvent, reaction temperature and other conditions, the reaction is carried through generally in 30 minutes to 16 hours and preferably in 1 to 8 hours. The resulting object compound of the invention can be isolated and purified by the known procedures mentioned hereinbefore.

By way of example, saikosaponin $b_2$ is dissolved in 10 to 50 ml/g, preferably 20 to 30 ml/g, of pyridine and PC is added thereto gradually while the temperature of the solution is maintained generally at $-70°$ C. to 0° C. and preferably at $-40°$ C. to $-10°$ C. Although the required amount of PC is of course dependent on the desired species of product compound, PC is used in a proportion of generally 1 to 10 equivalents, preferably 1 to 3 equivalents, per phosphate ester to be formed. The mixture is stirred for 1 to 8 hours, at the end of which time water or an aqueous alkali solution such as aqueous sodium hydrogen carbonate solution is added, whereby the phosphate ester of saikosaponin $b_2$ or a salt thereof is obtained. This product is generally a mixture of various phosphate esters of saikosaponin $b_2$ or salts thereof, and where the reaction product is in the form of the free acid, it can be converted in the conventional manner to a salt using, for example, an aqueous alkali solution and, then, be fractionated and purified by column chromatography using a reverse phase support such as chemically bound silica gel, e.g. $C_8$, $C_{18}$ and so on. Where LiChroprep RP-8 or RP-18 is used as said support, there can be isolated the salt of saikosaponin $b_2$-cyclic 16,28:4″,6″-bis(hydrogen phosphate)-23-(dihydrogen phosphate) from the fraction eluted with 3–30% (v/v), preferably 3–8% (v/v) aqueous acetonitrile, the salt of saikosaponin $b_2$-cyclic 16,28:4″,6″-bis(hydrogen phosphate) from the fraction eluted with 10–40% (v/v), preferably 10–18% (v/v) aqueous acetonitrile, and the salt of saikosaponin $b_2$-cyclic 4″,6″-(hydrogen phosphate) from the fraction eluted with 20–50% (v/v), preferably 20–30% (v/v) aqueous acetonitrile.

The phosphorylation of saikosaponin $b_1$ with PC in the same manner as described for saikosaponin $b_2$ gives rise to the phosphate ester of saikosaponin $b_1$ or a salt thereof. This reaction product is usually a mixture of various phosphate esters of saikosaponin $b_1$ or salts thereof, and where the reaction product is in the form of free acid, it can be converted in the conventional manner to a salt form using, for example, an aqueous alkali solution and, then, be fractionated and purified by column chromatography using LiChroprep RP-8 or RP-18 as the support. In this case, there can be isolated the salt of saikosaponin $b_1$-cyclic 16,28:4″,6″-bis(hydrogen phosphate)-23-(dihydrogen phosphate) from the fraction eluted with 3–30% (v/v), preferably 3–8% (v/v) aqueous acetonitrile, the salt of saikosaponin $b_1$-cyclic 16,28:4″,6″-bis(hydrogen phosphate) from the fraction eluted with 10–40% (v/v), preferably 10–18% (v/v) aqueous acetonitrile, and the salt of saikosaponin $b_1$-cyclic 4″,6″-(hydrogen phosphate) from the fraction eluted with 20–50% (v/v), preferably 20–30% (v/v) aqueous acetonitrile.

The phosphorylation of saikosaponin h with PC in the same manner as described for saikosaponin $b_2$ gives rise to the phosphate ester of saikosaponin h or a salt thereof. This reaction product is usually a mixture of various phosphate esters of saikosaponin h or salts thereof, and where the reaction product is in the form of free acid, it can be converted in the conventional manner to a salt form using, for example, an aqueous alkali solution and, then, be fractionated and purified by column chromatography using LiChroprep RP-8 or RP-18 as the support. In this case, there can be isolated the salt of saikosaponin h-cyclic 16,28:4‴,6‴-bis(hydrogen phosphate) from the fraction eluted with 3–20% (v/v), preferably 3–8% (v/v) aqueous acetonitrile and the salt of saikosaponin h-cyclic 4''',6'''-(hydrogen phosphate) from the fraction eluted with 10–30% (v/v), preferably 10–18% (v/v) aqueous acetonitrile.

The phosphorylation of saikosaponin a with PC in the same manner as described for saikosaponin $b_2$ gives rise to the phosphate ester of saikosaponin a or a salt thereof. This reaction product is usually a mixture of various phosphate esters of saikosaponin a or salts thereof, and where the reaction product is in the form of free acid, it can be converted in the conventional manner to a salt form using, for example, an aqueous alkali solution and, then, be fractionated and purified by column chromatography using LiChroprep RP-8 or RP-18 as the support. In this case, there can be isolated the salt of saikosaponin a-cyclic 4'',6''-(hydrogen phosphate)-23-(dihydrogen phosphate) from the fraction eluted with 3–30% (v/v), preferably 3–8% (v/v) aqueous acetonitrile, and the salt of saikosaponin a-cyclic 4'',6''-(hydrogen phosphate) from the fraction eluted with 10–40% (v/v), preferably 10–15% (v/v) aqueous acetonitrile.

The phosphorylation of saikosaponin d with PC in the same manner as described for saikosaponin $b_2$ gives rise to the phosphate ester of saikosaponin d or a salt thereof. This reaction product is usually a mixture of various phosphate esters of saikosaponin d or salts thereof, and where the reaction product is in the form of free acid, it can be converted in the conventional manner to a salt form using, for example, an aqueous alkali solution and, then, be fractionated and purified by column chromatography using LiChroprep RP-8 or RP-18 as the support. In this case, there can be isolated the salt of saikosaponin d-cyclic 4'',6''-(hydrogen phosphate)-23-(dihydrogen phosphate) from the fraction eluted with 3–30% (v/v), preferably 3–8% (v/v) aqueous acetonitrile and the salt of saikosaponin d-cyclic 4'',6''-(hydrogen phosphate) from the fraction eluted with 15–40% (v/v), preferably 15–25% (v/v) aqueous acetonitrile.

The phosphorylation of saikosaponin c with PC in the same manner as described for saikosaponin $b_2$ gives rise to saikosaponin c-cyclic 4''',6'''-(hydrogen phosphate) or a salt thereof.

Where the object compound of the invention, the phosphate ester of saikosaponin a, $b_1$, $b_2$, c or d or saikogenin A, C or D is in the form of a free acid, it may be converted to a salt with an alkali metal or alkaline earth metal, such as sodium, potassium, calcium, etc., in the conventional manner, though an eluent used in chromatography for isolating the object compound varies based on pH condition of the conversion (in the above Production Processes (1) and (5), the kind of eluent is described with proviso that pH of the reaction mixture is ca. 7.0–8.0).

Saikosaponin a, $b_1$, $b_2$, c, d and h and saikogenin A, C and D, and salts thereof which are used as starting materials in Production Processes (1) through (5) described above are known compounds and can be prepared by the processes described in Tetrahedron 24, 675 (1968) and other literature or by processes analogous thereto.

The phosphate esters of saikosaponin a, $b_1$, $b_2$, c, d and h and of saikogenin A, C and D, as well as salts thereof, which are provided by the present invention, exhibit potent antiinflammatory activity against adjuvant arthritis and can be used safely as drugs, for example as drugs for the treatment and prevention of rheumatism.

The phosphate esters and salts according to the invention can be used either singly or in admixture or in combination with other antiinflammatory agents, if necessary supplemented with auxiliary agents such as stabilizers, dispersing agents and so on, in such dosage forms as capsules, tablets, powders, solutions, suspensions, elixirs and so on to be formed in the conventional manner. These preparations can be administered by the oral route.

The daily dosage of the phosphate esters or salts according to the invention depends on the patient's condition and body weight, method of administration, and other factors but for adults, they can be appropriately administered orally in a daily dose of about 0.1 to 100 mg, preferably 0.2 to 4 mg per kilogram body weight in 1 to 3 divided doses.

The compound of the present invention exhibits efficacy against rat adjuvant arthritis which is an animal model of rheumatism and finds application in useful drugs with low risks of adverse reactions, for example as an antirheumatic drug. Furthermore, by rendering saikosaponins more readily soluble in water, the invention provides a pharmaceutical advantage.

The following examples are intended to describe the production processes for phosphate esters of saikosaponins and saikogenins or salts thereof of the invention in further detail. It should be understood, however, that the invention is by no means limited to these specific examples.

In the examples, column chromatography was performed under monitoring of the eluate by thin-layer chromatography (TLC). TLC was carried out using RP-8 $F_{254}S$ (manufactured by Merck and Co., Inc.) as the TLC plate and acetonitrile-water (ratio by volume 40:60) as the developer solvent by the ascending method. An UV detector and/or the method of spraying the plate with anisaldehyde-sulfuric acid reagent and developing the color by heating was employed. As the support for column chromatography, LiChroprep RP-8 or RP-18 (manufactured by Merck and Co., Inc.) was used. In $^{13}C$-nuclear magnetic resonance (NMR) spectrometry, sodium 2,2-dimethyl-2-silapentane-5-sulfonate and tetramethylsilane were used as internal standards for determinations in deuterium oxide and deuteriated pyridine, respectively. As the NMR spectrometer, JNM-GX-400 spectrometer (manufactured by JEOL, Ltd in JAPAN) was used and the δ values were shown in ppm. The symbols used in the examples have the following meanings. g: gram, mg: milligram, ml: milliliter, 1M: 1 molar concentration, w/v: weight/volume, w/w: w/w: weight/weight, v/v: volume/volume.

EXAMPLE 1

Production of trisodium saikosaponin $b_2$-23,28,6''-tris(dihydrogen phosphate) (1), disodium saikosaponin $b_2$-28,6''-bis(dihydrogen phosphate) (2), disodium saikosaponin $b_2$-23,6''-bis(dihydrogen phosphate) (3), and sodium saikosaponin $b_2$-6''-(dihydrogen phosphate) (4)

Saikosaponin $b_2$ (10.2 g) was dissolved in tetrahydrofuran (200 ml) and a solution of diphosphoryl chloride (DPC) (9.90 g) in tetrahydrofuran (30 ml) was added dropwise with stirring at −20° C. The mixture was further stirred at −20° C. for 40 minutes. The reaction mixture was poured in ice-water and adjusted to pH 7.5 with 1M aqueous sodium hydrogen carbonate solution, and the tetrahydrofuran was distilled off under reduced pressure. The residue was subjected to LiChroprep RP-8 column chromatography. As a result, there were isolated 1 (4.33 g) from the fraction eluted with water, 2 (0.64 g) from the acetonitrile-water (1:99) fraction, 3 (5.41 g) from the acetonitrile-water (5:95) fraction, and 4 (1.84 g) from the acetonitrile-water (18:82) fraction.

EXAMPLE 2

Production of trisodium saikosaponin $b_1$-cyclic 16,28-(hydrogen phosphate)-23,6''-bis(dihydrogen phosphate) (5), disodium saikosaponin $b_1$-cyclic 16,28-(hydrogen phosphate)-6'''-(dihydrogen phosphate) (6), and sodium saikosaponin $b_1$-cyclic 16,28-(hydrogen phosphate) (7)

Saikosaponin $b_1$ (3.65 g) was dissolved in tetrahydrofuran (100 ml) and a solution of DPC (3.53 g) in tetrahydrofuran (5 ml) was added dropwise with constant stirring at $-15°$ C. The mixture was further stirred at $-15°$ C. for 1 hour. The reaction mixture was poured in ice-water and adjusted to pH 7.5 with 1M aqueous sodium hydrogen carbonate solution, and the tetrahydrofuran was distilled off. The residue was subjected to LiChroprep RP-8 column chromatography. As a result, there were isolated 5 (0.56 g) from the aqueous fraction, 6 (1.00 g) from the acetonitrile-water (5:95) fraction, and 7 (1.36 g) from the acetonitrile-water (20:80) fraction.

EXAMPLE 3

Production of disodium saikosaponin a-23,6''-bis(dihydrogen phosphate) (8) and sodium saikosaponin a-6''-(dihydrogen phosphate) (9)

Saikosaponin a (2.04 g) was dissolved in tetrahydrofuran (40 ml) and a solution of DPC (3.29 g) in tetrahydrofuran (10 ml) was added dropwise with constant stirring at $-30°$ C. The mixture was further stirred at $-30°$ C. for 2 hours. The reaction mixture was poured in ice-water and adjusted to pH 7.5 with 1M aqueous sodium hydrogen carbonate solution, and the tetrahydrofuran was distilled off. The residue was subjected to LiChroprep RP-8 column chromatography. As a result, there were isolated 8 (0.93 g) from the acetonitrile-water (2:98) fraction and 9 (1.33 g) from the acetonitrile-water (8:92) fraction.

EXAMPLE 4

Production of sodium saikosaponin $b_1$-6''-(dihydrogen phosphate) (10)

Sodium saikosaponin a-6''-(dihydrogen phosphate) (9) (612 mg) was dissolved in 4% (w/v) aqueous hydrochloric acid and the solution was allowed to stand at room temperature (25° C.) overnight. The reaction mixture was neutralized with 1M aqueous sodium hydrogen carbonate solution and, then, purified by LiChroprep RP-18 column chromatography (eluent:acetonitrile-water 5:95) to recover the object compound (10) (286 mg).

EXAMPLE 5

Production of disodium saikosaponin $b_1$-23,6''-bis(dihydrogen phosphate) (11)

Disodium saikosaponin a-23,6''-bis(dihydrogen phosphate) (8) (3.80 g) was dissolved in 4% (w/v) hydrochloric acid (90 ml) and the solution was allowed to stand at room temperature (25° C.) for 5 hours. The reaction mixture was then neutralized with 1M aqueous sodium hydrogen carbonate solution and purified by LiChroprep RP-8 column chromatography (eluent:acetonitrile-water 5:95). The procedure gave the object compound (11) (2.33 g).

EXAMPLE 6

Production of disodium saikosaponin d-23,6''-bis(dihydrogen phosphate) (12)

Saikosaponin d (12.0 g) was dissolved in tetrahydrofuran (400 ml) and a solution of DPC (19.4 g) in tetrahydrofuran (100 ml) was added dropwise with constant stirring at $-30°$ C. The mixture was further stirred at $-30°$ C. for 2 hours. The reaction mixture was poured in ice-water and adjusted to pH 7.5 with 1M aqueous sodium hydrogen carbonate solution and the tetrahydrofuran was distilled off. The residue was subjected to LiChroprep RP-18 column chromatography. As a result, there was isolated 12 (10.9 g) from the acetonitrile-water (1:99) fraction.

EXAMPLE 7

Production of trisodium saikosaponin h-cyclic-16,28-(hydrogen phosphate)-3'',6'''-bis(dihydrogen phosphate) (13) and sodium saikosaponin h-cyclic-16,28-(hydrogen phosphate) (14)

Saikosaponin h (2.01 g) was dissolved in tetrahydrofuran (50 ml) and a solution of DPC (1.64 g) in tetrahydrofuran (10 ml) was added dropwise with constant stirring at $-30°$ C. The mixture was further stirred at $-30°$ C. for 45 minutes. The reaction mixture thus obtained was poured in ice-water and adjusted to pH 7.5 with 1M aqueous sodium hydrogen carbonate solution and the tetrahydrofuran was distilled off under reduced pressure. The residue was subjected to LiChroprep RP-18 column chromatography. As a result, there were isolated 13 (253 mg) from the acetonitrile-water (2:98) fraction and 14 (800 mg) from the acetonitrile-water (8:92) fraction.

EXAMPLE 8

Production of disodium saikosaponin c-cyclic-2'',3''-(hydrogen phosphate)-6'''-(dihydrogen phosphate) (15) and sodium saikosaponin c-6'''-(dihydrogen phosphate) (16)

Saikosaponin c (2.00 g) was dissolved in tetrahydrofuran (80 ml) and a solution of DPC (2.72 g) in tetrahydrofuran (10 ml) was added dropwise with constant stirring at $-30°$ C. The mixture was further stirred at $-30°$ C. for 1 hour. The reaction mixture thus obtained was poured in ice-water and adjusted to pH 7.5 with 1M aqueous sodium hydrogen carbonate solution and the tetrahydrofuran was distilled off under reduced pressure. The residue was subjected to LiChroprep RP-18 column chromatography. As a result, there were isolated 15 (0.40 g) from the acetonitrile-water (2:98) fraction and 16 (1.14 g) from the acetonitrile-water (15:85) fraction.

EXAMPLE 9

Production of disodium saikosaponin h-3'',6'''-bis(dihydrogen phosphate) (17)

Disodium saikosaponin c-cyclic 2'',3''-(hydrogen phosphate)-6'''-(dihydrogen phosphate) (15) (165 mg) was dissolved in 4% (w/v) hydrochloric acid (10 ml) and the solution was allowed to stand at room temperature (25° C.) overnight. The reaction mixture was neutralized with 1M aqueous sodium hydrogen carbonate solution and, then, purified by LiChroprep RP-18 column chromatography (eluent:acetonitrile-water 1.5:98.5) to recover the object compound (17) (74 mg).

EXAMPLE 10

Production of sodium saikosaponin h-6'''-(dihydrogen phosphate) (18)

Sodium saikosaponin c-6'''-(dihydrogen phosphate) (16) (623 mg) was dissolved in 4% (w/v) hydrochloric acid (25 ml) and the solution was allowed to stand at room temperature (25° C.) for 6 hours. The reaction mixture was neutralized with 1M aqueous sodium hydrogen carbonate solution and, then, purified by LiChroprep RP-18 column chromatography (eluent:acetonitrile-water 3:97) to recover the object compound (18) (334 mg).

EXAMPLE 11

Production of disodium saikogenin D-23,28-bis(dihydrogen phosphate) (19) and disodium saikogenin D-cyclic 3,23-(hydrogen phosphate)-28-(dihydrogen phosphate) (20)

Saikogenin D (2.95 g) was dissolved in tetrahydrofuran (150 ml) and a solution of DPC (31.5 g) in tetrahydrofuran (50 ml) was added dropwise with constant stirring at $-10°$ C. The mixture was further stirred at $-10°$ C. for 10 minutes. The reaction mixture was poured in ice-water and adjusted to pH 7.5 with 1M aqueous sodium hydrogen carbonate solution and the tetrahydrofuran was distilled off under reduced pressure. The residue was purified by LiChroprep RP-8 column chromatography (eluent:water) to recover a mixture (3.21 g) of 19 and 20.

EXAMPLE 12

Production of sodium saikosaponin $b_2$-23-(dihydrogen phosphate) (21)

Saikosaponin $b_2$ (10.0 g) was suspended in 2,2-dimethoxypropane (300 ml) followed by addition of p-toluenesulfonic acid (1.0 g). The mixture was stirred at room temperature (22° C.) for 3.5 hours. The reaction mixture thus obtained was poured into 1M aqueous sodium hydrogen carbonate solution for neutralization and the 2,2-dimethoxypropane was distilled off under reduced pressure. After addition of water, the resulting precipitate of diisopropylidenesaikosaponin $b_2$ was collected by filtration. This white powder (11.2 g) was dissolved in tetrahydrofuran (400 ml) and a solution of DPC (27 g) in tetrahydrofuran (200 ml) was added dropwise with constant stirring at $-30°$ C. The mixture was further stirred at $-30°$ C. for 3 hours. The reaction mixture was then poured in ice-water and allowed to stand for 3 hours for hydrolysis. The solution was then adjusted to pH 7.5 with 1M aqueous sodium hydroxide solution. Finally the tetrahydrofuran was distilled off under reduced pressure and the residue was purified by LiChroprep RP-8 column chromatography (eluent:acetonitrile-water 25:75) to recover the object compound (21) (5.4 g).

EXAMPLE 13

Production of sodium saikosaponin a-23-(dihydrogen phosphate) (22)

Saikosaponin a (1.00 g) was suspended in 2,2-dimethoxypropane (20 ml) followed by addition of p-toluenesulfonic acid (50 mg). The mixture was stirred at 0° C. for 8 hours. The reaction mixture thus obtained was poured into 1M aqueous sodium hydrogen carbonate solution for neutralization and the 2,2-dimethoxypropane was distilled off under reduced pressure. After addition of water, the resulting precipitate of isopropylidenesaikosaponin a was collected by filtration. This white powder (1.10 g) was dissolved in tetrahydrofuran (50 ml) and a solution of DPC (2.52 g) in tetrahydrofuran (50 ml) was added dropwise with constant stirring at $-30°$ C. The mixture was further stirred at $-30°$ C. for 2 hours. The reaction mixture was then poured in ice-water and allowed to stand for 1 hour for hydrolysis, after which it was adjusted to pH 7.5 with 1M aqueous sodium hydroxide solution. Finally the tetrahydrofuran was distilled off under reduced pressure and the residue was purified by LiChroprep RP-18 column chromatography (eluent:acetonitrile-water 20:80) to recover the object compound (22) (300 mg).

EXAMPLE 14

Production of sodium saikosaponin $b_1$-23-(dihydrogen phosphate) (23)

Saikosaponin a (1.00 g) was suspended in 2,2-dimethoxypropane (30 ml) followed by addition of p-toluenesulfonic acid (50 mg). The mixture was stirred at room temperature (22° C.) overnight. The reaction mixture thus obtained was poured into 1M aqueous sodium hydrogen carbonate solution for neutralization and the 2,2-dimethoxypropane was distilled off under reduced pressure. After addition of water, the resulting precipitate (1.10 g) of diisopropylidenesaikonsaponin $b_1$ was collected by filtration. This white powder (0.50 g) was dissolved in tetrahydrofuran (50 ml) and a solution of DPC (2.88 g) in tetrahydrofuran (50 ml) was added dropwise with constant stirring at 5° C. The mixture was further stirred at 5° C. for 3 hours. The reaction mixture was then poured in ice-water and allowed to stand for 1 hour for hydrolysis, after which it was adjusted to pH 7.5 with 1M aqueous sodium hydroxide solution. Finally the tetrahydrofuran was distilled off under reduced pressure and the residue was purified by LiChroprep RP-18 column chromatography (eluent:acetonitrile-water 25:75) to recover the object compound (23) (130 mg).

EXAMPLE 15

Production of sodium saikosaponin $b_2$-28-(dihydrogen phosphate) (24)

Saikosaponin d (4.00 g) was dissolved in pyridine (50 ml) followed by addition of acetic anhydride (50 ml). The mixture was allowed to stand overnight. The reaction mixture thus obtained was poured in ice-water and the resulting white precipitate was recovered by filtration. This powder (5.68 g) was dissolved in acetonitrile (100 ml) followed by addition of 5% (w/w) aqueous ferric chloride solution (75 ml). The mixture was stirred at room temperature (25° C.) for 8 hours. The resulting precipitate was recovered by filtration. Then, this powder (4.77 g) was dissolved in tetrahydrofuran (100 ml) and a solution of DPC (10.8 g) in tetrahydrofuran (35 ml) was added dropwise with constant stirring at $-30°$ C. The mixture was further stirred at $-30°$ C. for 3 hours. The reaction mixture was poured in ice-water and after adjustment to pH 13 with 1M aqueous sodium hydroxide solution, the mixture was stirred at room temperature (25° C.) for 2 hours. The reaction mixture was adjusted to pH 7.5 with 1M hydrochloric acid and the tetrahydrofuran was distilled off. Finally the residue was subjected to LiChroprep RP-18 column chromatography (eluent:acetonitrile-water 18:82) to recover the object compound (24) (2.62 g).

EXAMPLE 16

Production of disodium saikosaponin b$_2$-cyclic 16,28:4″,6″-bis(hydrogen phosphate) (25) and sodium saikosaponin b$_2$-cyclic 4″,6″-(hydrogen phosphate) (26)

Saikosaponin b$_2$ (4.00 g) was dissolved in pyridine (120 ml) and a solution of phosphorus oxychloride (PC) (0.94 g) in pyridine (30 ml) was added dropwise with constant stirring at $-30°$ C. The mixture was further stirred at $-30°$ C. for 2 hours. The reaction mixture was poured in ice-water, and the pyridine was distilled off under reduced pressure, and the residue was adjusted to pH 7.5 with 1M aqueous sodium hydrogen carbonate solution. This solution was subjected to LiChroprep RP-8 column chromatography. As a result, there were isolated 25 (0.50 g) from the acetonitrile-water (15:85) fraction and 26 (2.40 g) from the acetonitrile-water (25:75) fraction.

EXAMPLE OF CLINICAL STUDY

Using rats (18 animals), adjuvant (B. butyricum) was injected intradermally into a single hindpaw. The treated animals were divided into 3 groups of 6 individuals and disodium saikosaponin b$_2$-23,6″-bis(dihydrogen phosphate) (3) and sodium saikosaponin b$_2$-6″-(dihydrogen phosphate) (4) were orally administered in a dose of 50 mg/kg once a day for 14 consecutive days to one group and another group, respectively. The remaining group was left untreated for use as a control group. In all groups, the volume of the untreated hindpaw was determined 14 days after completion of treatment and the inhibitory effects on adjuvant arthritis were investigated in the groups treated with (3) and (4) in comparison with the control group. As a result, the rates of inhibition were 78% and 70%, respectively.

TABLE 1

$^{13}$C-NMR chemical shifts of saikosaponin b$_2$ phosphate ester derivatives (1–4, 21, 24–26): δ (ppm)

| C | 1 | 2 | 3 | 4 | 21 | 24* | 25 | 26 |
|---|---|---|---|---|---|---|---|---|
| 1 | 40.3 | 40.4 | 40.4 | 40.6 | 40.5 | 38.3 | 40.9 | 40.6 |
| 2 | 27.1 | 27.2 | 26.9 | 27.5 | 26.9 | 25.9 | 27.8 | 27.4 |
| 3 | 85.9$^{(a)}$ | 86.1$^{(a)}$ | 85.8$^{(a)}$ | 85.9$^{(a)}$ | 85.6$^{(a)}$ | 81.8 | 85.5$^{(a)}$ | 85.7$^{(a)}$ |
| 4 | 44.9 | 45.0 | 44.8 | 45.2 | 44.8 | 43.6 | 45.3 | 45.1 |
| 5 | 49.5 | 49.5 | 49.5 | 50.1 | 49.9 | 47.3 | 49.9 | 50.3 |
| 6 | 20.1 | 20.1 | 20.0 | 20.5 | 20.2 | 18.1 | 20.6 | 20.5 |
| 7 | 33.0 | 32.6 | 32.7 | 33.2 | 33.1 | 32.1 | 34.6 | 33.5 |
| 8 | 43.2 | 42.9 | 43.2 | 43.2 | 43.2 | 41.1 | 42.4 | 43.2 |
| 9 | 55.9 | 56.0 | 55.7 | 56.0 | 55.8 | 53.9 | 57.2 | 56.0 |
| 10 | 38.6 | 38.6 | 38.6 | 38.8 | 38.8 | 36.4 | 38.9 | 38.8 |
| 11 | 130.1 | 129.1 | 129.5 | 129.1 | 129.4 | 126.7 | 129.1 | 129.0 |
| 12 | 128.2 | 128.2 | 128.0 | 128.1 | 128.0 | 126.0 | 127.7 | 128.0 |
| 13 | 138.4 | 138.5 | 138.8 | 138.8 | 139.0 | 137.1 | 138.9 | 138.9 |
| 14 | 43.5 | 43.5 | 43.4 | 43.7 | 43.6 | 41.8 | 43.6 | 43.7 |
| 15 | 34.1 | 34.2 | 33.9 | 34.4 | 34.2 | 31.5 | 35.2 | 34.5 |
| 16 | 71.3 | 70.9 | 70.8 | 71.0 | 71.0 | 67.4 | 83.6 | 71.1 |
| 17 | 45.9 | 45.8 | 46.4 | 46.6 | 46.6 | 44.0 | 47.5 | 46.6 |
| 18 | 134.2 | 133.9 | 133.1 | 133.6 | 133.3 | 131.2 | 134.8 | 133.6 |
| 19 | 40.9 | 40.8 | 41.1 | 41.3 | 41.2 | 38.9 | 41.1 | 41.2 |
| 20 | 34.5 | 34.7 | 34.6 | 34.7 | 34.7 | 32.5 | 38.6 | 34.8 |
| 21 | 36.7 | 36.7 | 36.8 | 37.1 | 37.1 | 35.6 | 36.6 | 37.2 |
| 22 | 26.5 | 26.7 | 25.9 | 26.2 | 26.2 | 24.6 | 25.8 | 26.5 |
| 23 | 67.9 | 66.4 | 67.7 | 66.8 | 68.2 | 64.1 | 66.2 | 67.0 |
| 24 | 14.7 | 14.5 | 14.8 | 14.6 | 14.9 | 13.1 | 14.5 | 14.6 |
| 25 | 21.0 | 20.9 | 21.4 | 21.1 | 21.3 | 18.8 | 21.1$^{(b)}$ | 21.1 |
| 26 | 19.3 | 19.3 | 19.5 | 19.7 | 19.6 | 17.1 | 21.0$^{(b)}$ | 19.7 |
| 27 | 24.2 | 24.8 | 24.1 | 24.6 | 24.4 | 21.8 | 31.2 | 24.7 |
| 28 | 68.1 | 68.0 | 66.3 | 67.3 | 66.7 | 67.7 | 75.2 | 67.5 |
| 29 | 27.2 | 27.5 | 27.5 | 27.6 | 27.6 | 25.0 | 28.6 | 27.6 |
| 30 | 34.4 | 34.6 | 35.1 | 35.0 | 35.0 | 32.4 | 35.3 | 35.0 |
| 1′ | 106.2 | 106.4 | 106.0 | 106.6 | 105.9 | 105.7 | 107.0 | 106.6 |
| 2′ | 72.9 | 72.7 | 72.7 | 73.0 | 72.7 | 71.4 | 72.9 | 72.8 |
| 3′ | 86.1$^{(a)}$ | 86.4$^{(a)}$ | 86.1$^{(a)}$ | 86.4$^{(a)}$ | 85.8$^{(a)}$ | 85.2 | 86.3$^{(a)}$ | 86.6$^{(a)}$ |
| 4′ | 73.7 | 73.2 | 73.6 | 73.5 | 74.0 | 71.7 | 73.6 | 73.8 |
| 5′ | 71.5 | 71.1 | 71.3 | 71.7 | 72.4 | 70.9 | 69.8 | 70.1 |
| 6′ | 18.5 | 18.7 | 18.6 | 18.7 | 18.8 | 17.1 | 18.9 | 18.8 |
| 1″ | 106.7 | 106.7 | 106.6 | 106.7 | 106.3 | 106.4 | 107.1 | 106.9 |
| 2″ | 76.5 | 76.3 | 76.4 | 76.5 | 76.3 | 75.6 | 72.9 | 73.0 |
| 3″ | 77.7 | 77.3 | 77.5 | 77.7 | 78.4$^{(b)}$ | 78.5$^{(a)}$ | 76.2 | 76.3 |
| 4″ | 73.1 | 73.0 | 72.9 | 73.0 | 73.0 | 72.0 | 80.5 | 80.3 |
| 5″ | 78.1 | 78.0 | 78.0 | 78.2 | 78.5$^{(b)}$ | 78.2$^{(a)}$ | 75.9 | 76.1 |
| 6″ | 65.3 | 65.1 | 65.2 | 65.5 | 63.5 | 62.6 | 69.1 | 69.1 |

*After conversion to the free phosphate ester, the determination was made in deuteriated pyridine. Other determinations were made using sodium salts in deuterium oxide.
$^{(a)}$, $^{(b)}$: The assignments may be interchangeable.

TABLE 2

$^{13}$C-NMR chemical shifts of saikosaponin b$_1$ and a phosphate ester derivatives (5–11, 22, 23): δ (ppm)

| C | 5 | 6 | 7* | 10* | 11 | 23 | 8 | 9* | 22 |
|---|---|---|---|---|---|---|---|---|---|
| 1 | 40.3 | 40.5 | 38.3 | 38.4$^{(a)}$ | 40.6 | 40.5 | 40.5 | 38.6 | 40.4 |
| 2 | 27.2 | 27.6 | 25.9 | 25.9 | 27.2 | 27.1 | 27.0 | 25.9$^{(a)}$ | 27.1 |

TABLE 2-continued $^{13}$C-NMR chemical shifts of saikosaponin b$_1$ and a phosphate ester derivatives (5–11, 22, 23): δ (ppm)

| C | 5 | 6 | 7* | 10* | 11 | 23 | 8 | 9* | 22 |
|---|---|---|---|---|---|---|---|---|---|
| 3 | 84.9(a) | 85.8(a) | 81.7 | 81.8 | 85.1(a) | 85.3 | 86.0 | 81.7 | 85.0(a) |
| 4 | 44.6 | 45.2 | 43.5 | 43.5 | 44.7 | 44.6 | 44.8 | 43.5 | 44.6 |
| 5 | 49.2 | 49.6 | 47.1 | 47.2 | 49.3 | 49.6 | 49.6 | 47.2 | 49.4 |
| 6 | 19.7 | 19.2 | 18.1 | 18.1 | 19.8 | 20.0 | 19.2 | 17.5 | 19.2 |
| 7 | 33.4 | 33.4 | 32.3 | 32.4 | 33.8 | 34.0 | 33.0 | 31.5 | 32.8 |
| 8 | 42.7 | 42.9 | 40.8 | 40.4 | 42.5 | 42.4 | 44.0 | 42.1 | 43.8 |
| 9 | 56.1 | 56.5 | 54.3 | 54.4 | 56.2 | 56.2 | 54.6 | 53.0 | 54.6 |
| 10 | 38.4 | 38.7 | 36.4 | 36.4 | 38.5 | 38.5 | 38.3 | 36.2 | 38.1 |
| 11 | 130.8 | 130.8 | 128.1 | 127.0 | 129.9 | 129.6 | 135.9 | 132.1 | 135.2 |
| 12 | 127.0 | 127.2 | 125.0 | 125.6 | 127.4 | 127.3 | 131.8 | 131.0 | 131.9 |
| 13 | 139.2 | 139.3 | 136.9 | 136.4 | 139.2 | 139.2 | 86.8 | 83.8 | 86.4 |
| 14 | 46.8 | 47.0 | 44.6 | 44.2(b) | 46.8 | 46.4 | 47.6 | 45.6 | 47.5 |
| 15 | 33.8 | 34.2 | 31.7 | 34.7(c) | 35.5 | 35.7 | 36.7 | 36.2 | 36.7 |
| 16 | 86.7 | 86.6 | 83.9 | 76.4 | 79.1 | 78.8 | 67.1 | 64.0 | 66.6 |
| 17 | 42.0 | 42.3 | 40.2 | 44.3(b) | 45.8 | 45.9 | 48.4 | 46.8 | 48.3 |
| 18 | 132.1 | 132.6 | 130.6 | 133.2 | 133.7 | 133.9 | 54.2 | 52.1 | 54.0 |
| 19 | 40.7 | 40.9 | 38.3 | 38.3(a) | 40.3 | 40.3 | 39.8 | 37.8 | 39.6 |
| 20 | 34.8 | 35.1 | 32.7 | 32.6 | 34.7 | 34.6 | 33.7 | 31.5 | 33.5 |
| 21 | 36.2 | 36.5 | 34.5 | 35.1(c) | 36.9 | 37.0 | 36.4 | 34.6 | 36.5 |
| 22 | 31.6 | 32.0 | 30.0 | 29.8 | 31.5 | 31.5 | 27.6 | 25.7(a) | 27.5 |
| 23 | 68.6 | 66.2 | 63.9 | 65.3 | 68.5 | 68.8 | 68.1 | 65.2 | 68.5 |
| 24 | 14.3 | 14.5 | 13.0 | 13.0 | 14.4 | 14.4 | 14.6 | 12.9 | 14.2 |
| 25 | 21.0 | 21.1 | 18.8 | 18.8 | 21.0 | 20.9 | 20.9 | 18.7 | 20.7 |
| 26 | 18.9 | 19.2 | 17.2 | 17.2 | 19.1 | 19.1 | 21.7 | 19.9 | 21.6 |
| 27 | 23.2 | 23.8 | 21.2 | 21.9 | 24.0 | 24.1 | 22.8 | 20.8 | 22.9 |
| 28 | 68.8 | 69.0 | 66.6 | 63.9 | 65.4 | 65.4 | 74.5 | 72.9 | 74.5 |
| 29 | 26.8 | 27.1 | 24.2 | 24.8 | 27.2 | 27.1 | 36.0 | 33.6 | 36.0 |
| 30 | 34.5 | 34.6 | 32.0 | 32.2 | 34.8 | 34.5 | 26.5 | 23.8 | 26.4 |
| 1' | 106.2 | 106.6 | 105.7 | 105.7 | 106.2 | 106.0 | 106.2 | 105.6 | 106.1 |
| 2' | 72.6 | 72.9 | 71.4 | 71.5 | 72.6 | 72.4 | 72.6 | 71.5 | 72.4 |
| 3' | 85.4(a) | 86.1(a) | 85.1 | 85.4 | 85.5(a) | 85.3 | 86.0 | 85.3 | 85.4(a) |
| 4' | 73.4 | 73.3 | 71.6 | 71.8 | 73.4 | 73.6 | 73.4 | 71.7 | 73.5 |
| 5' | 71.3 | 71.3 | 70.8 | 70.9 | 71.2 | 72.1 | 71.2 | 70.8 | 71.7 |
| 6' | 18.5 | 18.8 | 17.0 | 17.0 | 18.6 | 18.6 | 18.6 | 17.2 | 18.6 |
| 1" | 106.4 | 106.9 | 106.1 | 106.1 | 106.5 | 106.1 | 106.5 | 106.1 | 106.4 |
| 2" | 76.0 | 76.4 | 75.5 | 75.4 | 76.1 | 76.0 | 76.2 | 75.4 | 75.6 |
| 3" | 77.5 | 77.5 | 78.3(a) | 77.3 | 77.4 | 78.2 | 77.3 | 77.2 | 77.8 |
| 4" | 72.8 | 72.9 | 71.9 | 70.5 | 72.8 | 72.8 | 72.8 | 70.4 | 72.6 |
| 5" | 77.4 | 78.1 | 78.1(a) | 76.7 | 77.6 | 78.3 | 77.9 | 76.6 | 78.0 |
| 6" | 65.7 | 65.2 | 62.5 | 64.1 | 65.4 | 63.2 | 65.0 | 63.8 | 62.7 |

*After conversion to the free phosphate ester, the determination was made in deuterated pyridine. Other determinations were made using sodium salts in deuterium oxide.
(a), (b), (c): The assignments may be interchangeable.

TABLE 3

$^{13}$C-NMR chemical shifts of saikosaponin d and saikogenin D phosphate ester derivatives (12, 19 and 20): δ (ppm)

| C | 12 | 19 | 20 |
|---|---|---|---|
| 1 | 40.6 | 40.3 | 40.5 |
| 2 | 27.0 | 26.8 | 26.7 |
| 3 | 86.1(a) | 76.9 | 86.8 |
| 4 | 44.8 | 44.1 | 44.1 |
| 5 | 49.6 | 50.8 | 52.6 |
| 6 | 19.3 | 20.5 | 20.6 |
| 7 | 32.6 | 32.8 | 32.8 |
| 8 | 43.6 | 43.1 | 43.1 |
| 9 | 54.7 | 55.8 | 55.6 |
| 10 | 38.3 | 38.7 | 39.0 |
| 11 | 135.3 | 129.6 | 128.9 |
| 12 | 132.9 | 128.1 | 128.4 |
| 13 | 87.7 | 138.5 | 138.3 |
| 14 | 45.3 | 43.4 | 43.4 |
| 15 | 36.3 | 34.0 | 33.9 |
| 16 | 79.3 | 71.0 | 70.9 |
| 17 | 47.2 | 45.9 | 45.8 |
| 18 | 53.0 | 134.0 | 134.4 |
| 19 | 40.6 | 41.0 | 40.8 |
| 20 | 33.9 | 34.5 | 34.6 |
| 21 | 38.8 | 36.6 | 36.6 |
| 22 | 33.1 | 26.4 | 26.4 |
| 23 | 68.0 | 72.7 | 80.9 |
| 24 | 14.7 | 13.8 | 13.0 |
| 25 | 21.0 | 20.8 | 21.3 |
| 26 | 21.3 | 19.1 | 19.1 |
| 27 | 20.3 | 24.1 | 24.3 |
| 28 | 79.8 | 67.9 | 67.9 |
| 29 | 36.0 | 27.3 | 27.4 |
| 30 | 26.9 | 34.5 | 34.5 |
| 1' | 106.2 | | |
| 2' | 72.7 | | |
| 3' | 86.2(a) | | |
| 4' | 73.4 | | |
| 5' | 71.2 | | |
| 6' | 18.6 | | |
| 1" | 106.6 | | |
| 2" | 76.3 | | |
| 3" | 77.4 | | |
| 4" | 72.8 | | |
| 5" | 78.0 | | |
| 6" | 65.1 | | |

(a): The assignments may be interchangeable.

TABLE 4

$^{13}$C-NMR chemical shifts of saikosaponin h and c phosphate ester derivatives (13-18): δ (ppm)

| C | 13 | 14* | 17 | 18* | 15 | 16 |
|---|---|---|---|---|---|---|
| 1 | 40.4 | 38.3$^a$ | 40.8 | 38.4$^a$ | 41.0 | 41.0 |
| 2 | 28.2 | 26.3 | 28.1 | 26.3 | 27.9 | 27.8 |
| 3 | 93.2 | 88.9 | 92.9 | 88.9 | 93.2 | 92.8 |
| 4 | 41.5 | 39.5 | 41.5 | 39.5 | 41.5 | 41.5 |
| 5 | 57.6 | 55.1 | 57.8 | 55.2 | 58.1 | 58.1 |
| 6 | 19.0 | 18.3 | 19.1 | 18.3 | 20.1 | 20.1 |
| 7 | 34.2$^{(a)}$ | 32.5 | 34.6 | 32.6 | 34.1 | 34.3 |
| 8 | 42.9 | 40.7 | 42.6 | 40.3 | 44.1 | 44.2 |
| 9 | 56.4 | 54.1 | 56.5 | 54.1 | 55.2 | 55.2 |
| 10 | 38.8 | 36.4 | 38.4 | 36.4 | 38.5 | 38.6 |
| 11 | 131.6 | 128.0 | 129.9 | 127.0 | 136.2 | 135.9 |
| 12 | 127.3 | 125.0 | 127.6 | 125.6 | 131.6 | 132.1 |
| 13 | 139.2 | 136.8 | 138.9 | 136.3 | 86.9 | 86.6 |
| 14 | 46.9 | 44.5 | 46.0$^{(a)}$ | 44.2$^{(b)}$ | 47.7 | 47.8 |
| 15 | 33.7$^{(a)}$ | 31.7 | 35.7 | 34.7$^{(c)}$ | 37.0 | 37.4 |
| 16 | 87.2 | 83.8 | 78.9 | 76.5 | 67.0 | 66.9 |
| 17 | 42.3 | 40.2 | 46.4$^{(a)}$ | 44.3$^{(b)}$ | 48.5 | 48.5 |
| 18 | 133.0 | 130.7 | 134.4 | 133.3 | 54.0 | 54.1 |
| 19 | 40.6 | 38.1$^{(a)}$ | 40.8 | 38.0$^{(a)}$ | 40.1 | 40.2 |
| 20 | 34.9 | 32.7 | 34.8 | 32.6 | 33.8 | 33.7 |
| 21 | 36.4 | 34.5 | 36.9 | 35.1$^{(c)}$ | 36.5 | 36.8 |
| 22 | 31.8 | 30.0 | 31.6 | 29.9 | 27.3 | 27.4 |
| 23 | 29.8 | 27.9 | 29.9 | 27.9 | 30.1 | 30.2 |
| 24 | 18.2 | 16.4 | 18.2 | 16.4 | 18.1 | 18.2 |
| 25 | 20.5 | 18.3 | 20.6 | 18.3 | 20.1 | 20.2 |
| 26 | 19.4 | 16.9 | 19.3 | 16.9 | 21.8 | 21.9 |
| 27 | 23.5 | 21.2 | 24.2 | 22.0 | 23.5 | 23.4 |
| 28 | 69.2 | 66.6 | 65.3 | 63.9 | 74.4 | 74.6 |
| 29 | 26.6 | 24.2 | 27.1 | 24.8 | 36.3 | 36.2 |
| 30 | 34.8 | 32.0 | 34.7 | 32.3 | 26.3 | 26.3 |
| 1' | 107.4 | 106.4 | 107.5 | 106.4 | 107.6 | 107.3 |
| 2' | 76.1 | 74.9 | 75.8 | 75.1 | 76.2 | 76.2 |
| 3' | 77.2 | 76.6 | 77.6 | 76.7 | 77.6 | 77.5 |
| 4' | 80.3 | 79.6 | 80.9 | 80.4 | 81.1 | 80.8 |
| 5' | 76.4 | 75.3 | 76.4 | 75.4 | 76.2 | 76.4 |
| 6' | 72.1 | 68.9 | 72.1 | 69.2 | 71.7 | 71.1 |
| 1″ | 103.2 | 102.6 | 102.9 | 103.2 | 99.8 | 103.4 |
| 2″ | 72.9 | 72.1 | 72.6 | 71.8 | 80.2 | 74.7 |
| 3″ | 76.7 | 72.4 | 76.8 | 72.5 | 77.1 | 73.0 |
| 4″ | 74.9 | 73.6 | 74.7 | 73.5 | 75.0 | 75.7 |
| 5″ | 71.8 | 70.3 | 71.5 | 70.4 | 69.1 | 71.8$^{(a)}$ |
| 6″ | 19.4 | 18.2 | 19.3 | 18.2 | 18.8 | 19.3 |
| 1‴ | 106.0 | 104.8 | 106.3 | 104.5 | 106.1 | 105.6 |
| 2‴ | 76.1 | 74.6 | 75.8 | 74.7 | 76.0 | 76.2 |
| 3‴ | 77.9 | 78.0 | 77.6 | 77.6 | 78.2 | 78.2 |
| 4‴ | 71.8 | 71.4 | 71.5 | 71.0 | 71.4 | 71.9$^{(a)}$ |
| 5‴ | 78.3 | 78.0 | 78.3 | 76.7 | 78.3 | 77.9 |
| 6‴ | 65.1 | 62.4 | 65.3 | 65.6 | 65.3 | 66.4 |

*After conversion to the free phosphate ester, the determination was made in deuterated pyridine. Other determinations were made using sodium salts in deuterium oxide.
$^{(a)}$, $^{(b)}$, $^{(c)}$: The assignments may be interchangeable.

What is claimed is:

1. A phosphate ester of saikosaponin a, $b_1$, $b_2$, c, d or h or a pharmaceutically acceptable salt thereof.

2. A compound as claimed in claim 1, which is a phosphate ester of saikosaponin a or d, having the formula:

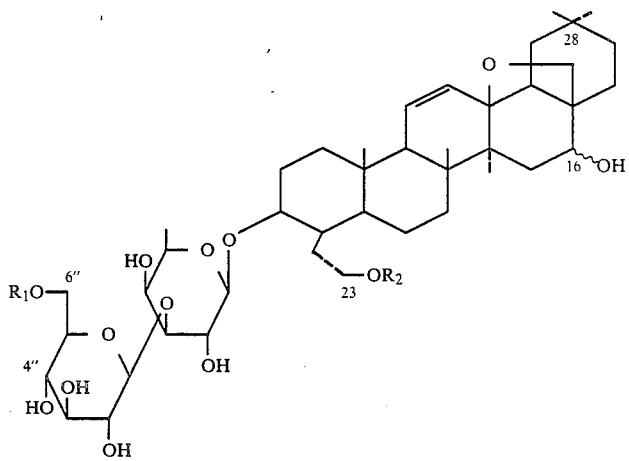

wherein $R_1$ and $R_2$ each is a hydrogen atom or a phosphono group, provided that both cannot be hydrogen atoms and further provided that the phosphono group $R_1$ can join with the hydroxyl group in the 4″ position to form a cyclic phosphate ester, or a pharmaceutically acceptable salt thereof.

3. A compound as claimed in claim 1, which is a phosphate ester of saikosaponin c, having the formula:

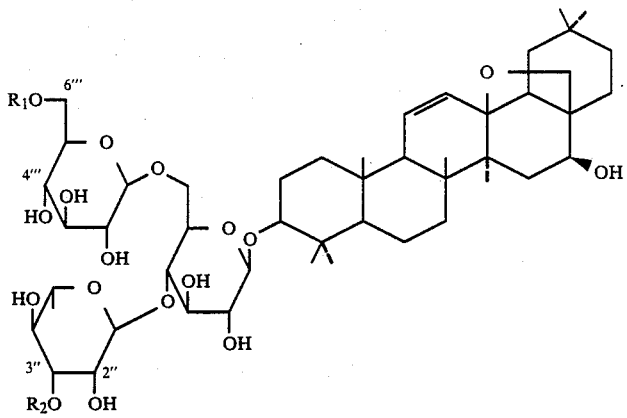

wherein $R_1$ and $R_2$ each is a hydrogen atom or a phosphono group, provided that both cannot be hydrogen atoms and further provided that the phosphono groups $R_1$ and $R_2$ can join with the hydroxyl groups in the 4''' and 2'' positions, respectively, to form a cyclic phosphate ester each, or a pharmaceutically acceptable salt thereof.

4. A compound as claimed in claim 1, which is a phosphate ester of saikosaponin $b_1$ or $b_2$, having the formula:

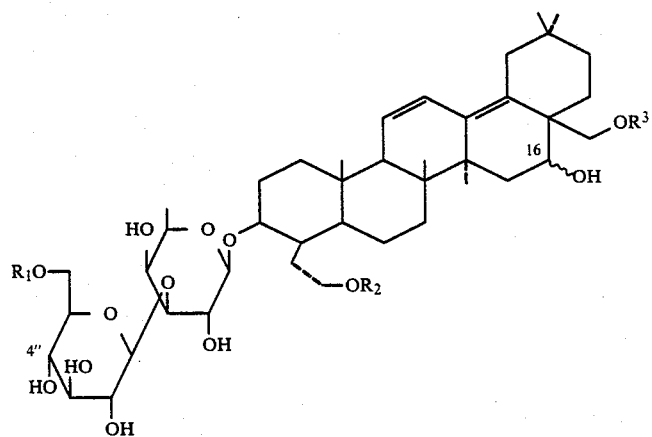

wherein $R_1$, $R_2$ and $R_3$ each is a hydrogen atom or a phosphono group, provided that all of them cannot be hydrogen atoms and further provided that the phosphono groups $R_1$ and $R_3$ can join with the hydroxyl groups in the 4'' and 16 positions, respectively, to form a cyclic phosphate ester each, or a pharmaceutically acceptable salt thereof.

5. A compound as claimed in claim 1, which is a phosphate ester of saikosaponin h, having the formula:

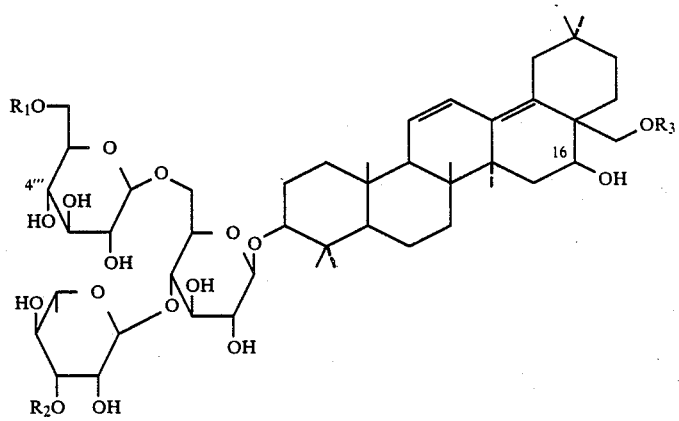

wherein $R_1$, $R_2$ and $R_3$ each is a hydrogen atom or a phosphono group, provided that all of them cannot be hydrogen atoms and further provided that the phos-
phono groups $R_1$ and $R_3$ can join with the hydroxyl groups in the 4''' and 16 positions, respectively, to form a cyclic phosphate ester each, or a pharmaceutically acceptable salt thereof.

6. A compound as claimed in claim 1, which is saikosaponin $b_2$-23, 6''-bis(dihydrogen phosphate) or its sodium salt.

7. A compound as claimed in claim 1, which is saikosaponin $b_2$-6''-(dihydrogen phosphate) or its sodium salt.

8. A compound as claimed in claim 1, which is saikosaponin $b_2$-23-(dihydrogen phosphate) or its sodium salt.

9. An antiinflammatory composition against adjuvant arthritis which comprises an effective dose of a phosphate ester as claimed in claim 1, or a pharmaceutically acceptable salt thereof and a pharmaceutically acceptable carrier.

10. A compound of the group consisting of saikosaponin $b_2$-23, 6''-bis(dihydrogen phosphate),
 saikosaponin $b_2$-6''-(dihydrogen phosphate) and
 saikosaponin $b_2$-23-(dihydrogen phosphate) or
 a sodium salt thereof.

* * * * *